United States Patent [19]

Daher et al.

[11] 4,091,472
[45] May 30, 1978

[54] PROSTHETIC FOOT

[76] Inventors: Reinhard L. Daher, R.R. #1, Dugald, Canada, R0E0K0; Frederick Robert Tucker, 138 Buxton Road, Winnipeg,, Canada, R3T0G9

[21] Appl. No.: 754,501

[22] Filed: Dec. 27, 1976

[51] Int. Cl.² ............................................. A61F 1/08
[52] U.S. Cl. .................................................... 3/7
[58] Field of Search .......................................... 3/6–8, 3/2

[56] References Cited

U.S. PATENT DOCUMENTS

| | | | |
|---|---|---|---|
| 616,873 | 1/1899 | Andrews | 3/7 X |
| 3,098,239 | 7/1963 | Nader | 3/7 |
| 3,484,871 | 12/1969 | Orange | 3/7 |
| 3,766,569 | 10/1973 | Orange | 3/7 |
| 3,833,941 | 9/1974 | Wagner | 3/7 |

FOREIGN PATENT DOCUMENTS 1,434,413  5/1976  United Kingdom .................. 3/7

*Primary Examiner*—Ronald L. Frinks
*Attorney, Agent, or Firm*—Stanley G. Ade

[57] ABSTRACT

The foot comprises a keel of hard material such as wood and having a flat attachment surface, a curved instep portion and a planar diminished heel portion. Recesses are formed above and below the front ends of the toe portion and a resilient reinforcing tongue portion is secured within each recess. These tongues extend forwardly of the keel and are connected together with a relatively dense foamed plastic therebetween so that the resistance of the tongues and of the plastic controls the flexural resistance of the toe portion. The shape of the heel portion permits the maximum amount of foam possible to be provided at the heel so that the density of the heel is variable and controllable by the foaming process. The final foam process envelopes the keel with the exception of part of the flat top, in one-piece moulded rubber or synthetic plastic foam so processed as to produce a skin on the exterior surface. The thickness of foam at the rear upper area behind the flat upper surface of the keel is relatively small thus preventing any tendency of the keel to separate from the foam at this point.

16 Claims, 5 Drawing Figures

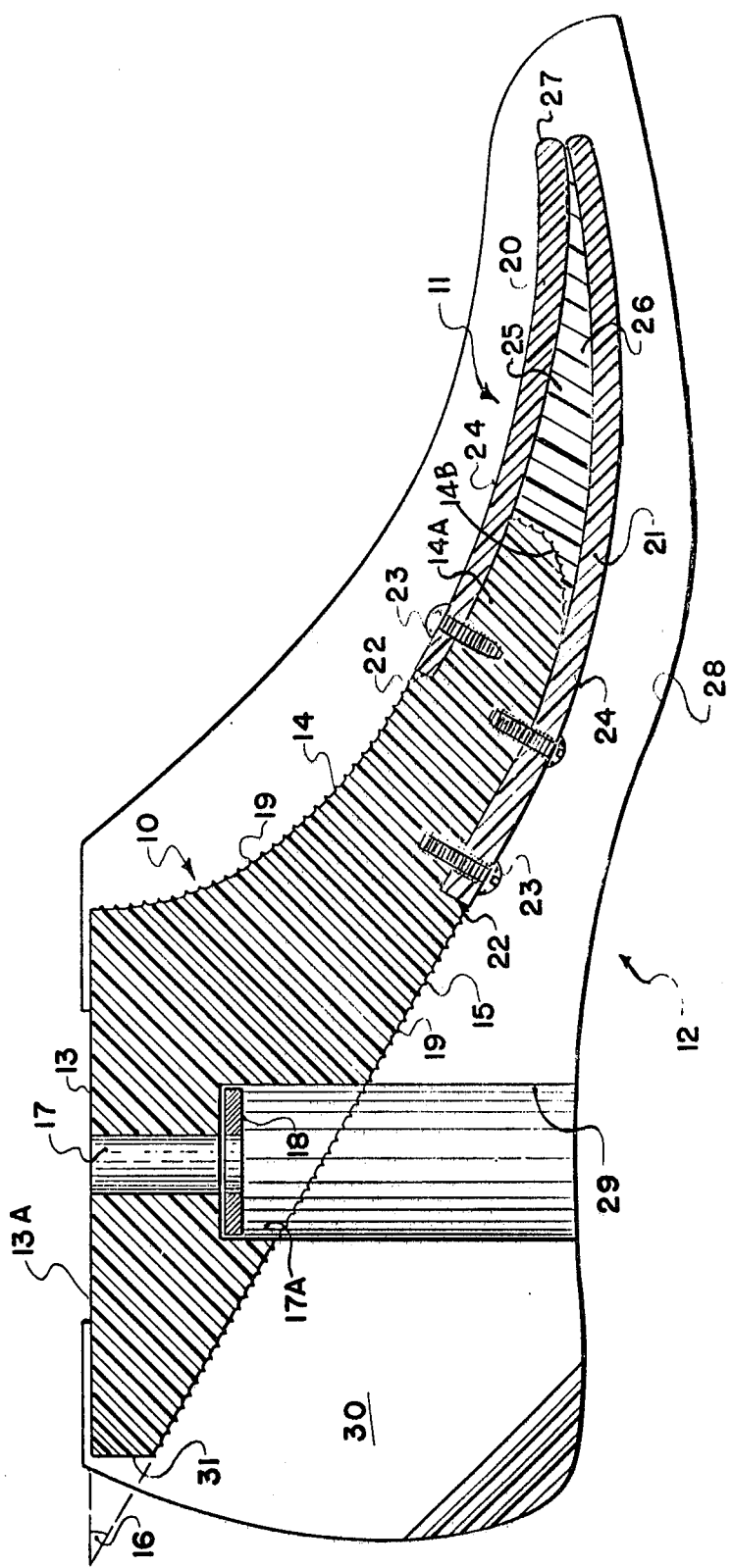

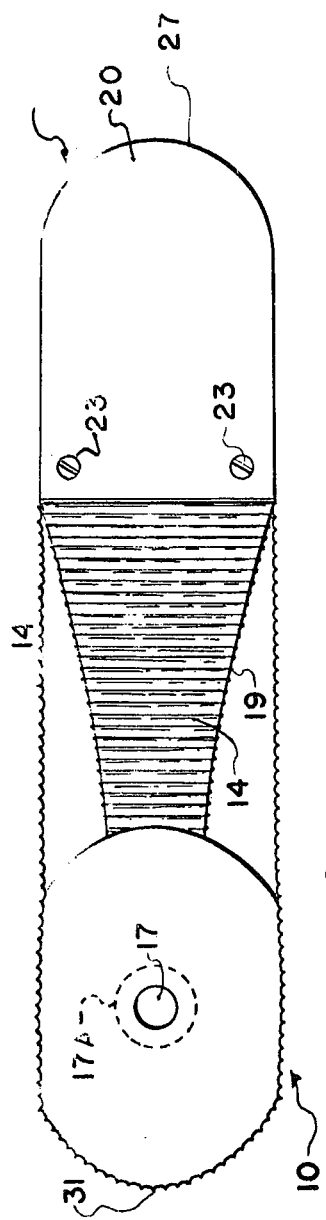
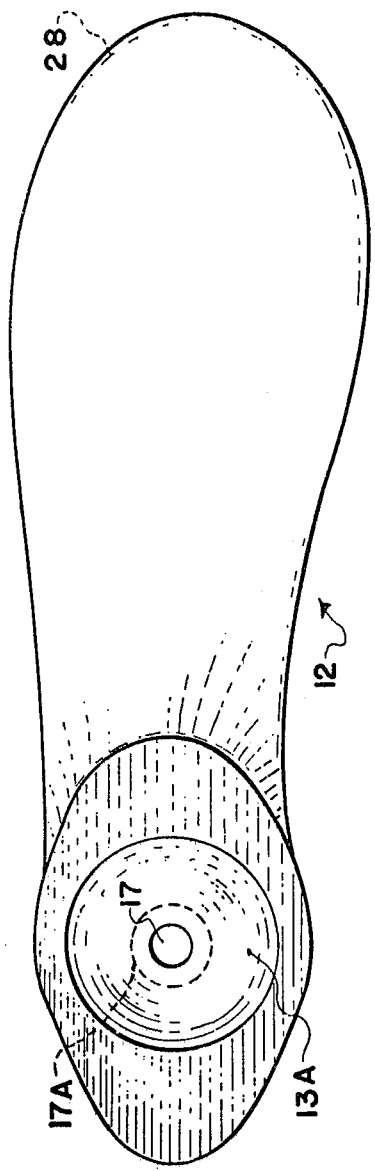
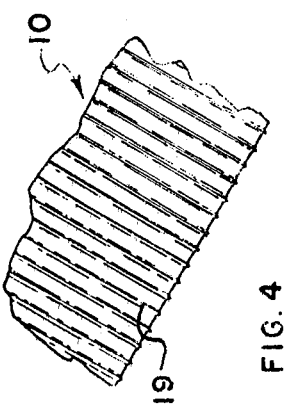
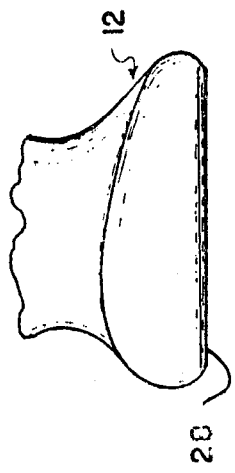

PROSTHETIC FOOT

BACKGROUND OF THE INVENTION

This invention relates to new and useful improvements in the manufacture and construction of prosthetic or artificial feet, particularly prosthetic feet known in the industry as the SACH (solid-ankle-cushion heel).

Conventionally, SACH feet include a keel with a single lower reinforcing belt or the like extending forwardly from a rigid keel in order to give some degree of resistance to dorsiflexion of the foot when in use.

One such device is illustrated in U.S. Pat. No. 3,098,239 in which the reinforcing belt extends from a keyway in the toe of the keel.

Such a system often gives insufficient control of the flexure of the toe area because of the difficulty of controlling the rigidity of this area.

Other SACH feet on the market utilize a foam covering over the keel which, because of the type of manufacture, shows a parting line half way up the finished foot which is unsightly; and some feet have a foam body portion surrounding the keel which, after some use, tends to detach therefrom particularly at the back of the heel portion of the keel.

SUMMARY OF THE INVENTION

The present invention overcomes these disadvantages by providing a keel of substantially rigid material which includes a substantially flat upper attachment portion, a concavely curved instep portion and diminished heel portion. A preformed toe assembly is secured to and extends forwardly from the front ends of the instep portion and the diminished heel portion and a one-piece flexible foam foot shaped body with exterior skin is moulded around the keel and surrounds and envelopes same and the toe assembly secured thereto. The toe assembly includes upper and lower flexible plate members secured by one end thereof to the front end of the keel and extends forwardly therefrom. The flexible plate members converge together at the distal ends thereof thereby defining a wedge shaped cavity which is filled with a relatively hard foam moulded therewithin which not only gives the requisite flexural resistance to the toe portion but also the desired upwardly curved shape.

The principal object and essence of the invention is therefore to provide a device of the character herewithin described in which the keel portion includes a toe assembly, the flexural characteristics of which are easily controlled depending upon design parameters.

Another object of the invention is to provide a device of the character herewithin described which includes a one-piece foot shaped cover or body portion formed of foamed rubber or synthetic plastic having a skin formed on the exterior thus giving a smooth finished surface.

Another object of the invention is to provide a device of the character herewithin described which enables the parting line to be at the junction between the sole portion and the body portion of the finished prosthetic foot, and thereby improving cosmesis by being out of sight from the side.

A yet further object of the invention is to provide a device of the character herewithin described which provides a foot which is hard wearing, substantially water repellant, and which permits easy donning and doffing of the associated shoe.

A still further object of the invention is to provide a device of the character herewithin described which is simple in construction, economical in manufacture and otherwise well suited to the purpose for which it is designed.

With the foregoing objects in view, and other such objects and advantages as will become apparent to those skilled in the art to which this invention relates as this specification proceeds, our invention consists essentially in the arrangement and construction of parts all as hereinafter more particularly described, reference being had to the accompanying drawings in which:

DESCRIPTION OF THE DRAWINGS

FIG. 1 is a longitudinal, cross sectional view of the finished foot.

FIG. 2 is a top plan view of the keel and toe portion per se.

FIG. 3 is a plan view of the finished foot.

FIG. 4 is an enlarged fragmentary side elevation of part of the keel showing the striations on the side wall thereof.

FIG. 5 is a partial front elevation of the finished foot showing the part line.

In the drawings like characters of reference indicate corresponding parts in the different figures.

DETAILED DESCRIPTION

Proceeding therefore to describe the invention in detail, reference should be made to the accompanying drawings which illustrates a keel collectively designated 10, having a toe assembly collectively designated 11 secured thereto, the keel and toe assembly then being enveloped within a foamed rubber or foamed plastic foot shaped body collectively designated 12.

In detail, the keel 10 is made preferably of a hard material such as a rigid plastic or wood and includes a planar upper attachment surface 13, a concavely curved instep portion 14 and what is defined as a diminishing heel portion or surface 15 which extends upwardly and rearwardly from the front end of the instep portion specifically designated 14A.

It will be noted that the diminished heel surface or portion 15 lies at an angle of approximately 30° from the horizontal as indicated by reference character 16, the purpose of which will hereinafter be described.

A vertical drilling 17 is formed through the keel substantially centrally of the planar upper surface 13 for attachment to an artificial leg or limb by means of a bolt (not illustrated) in conjunction with washer 18 in the conventional manner.

The side surfaces and part of the instep portion 14 are striated as illustrated by reference character 19 to facilitate the attachment of the body 12 when same is formed as will hereinafter be described. Also the nose 14B of the keel in striated to facilitate attachment of adjacent foam.

The toe assembly 11 comprises an upper flexible member or plate 20 and a lower flexible member or plate 21. These members or plates 20 and 21 may be manufactured from a flexible rigid plastic such as "nylon" or, alternatively, may be made from lengths of webbed belting or the like having considerable resistance yet at the same time having the desired flexibility.

These plates or belts are secured to the front portion of the instep portion 14 and the diminished heel portion 15 respectively and in this regard, transverse recesses 22 are provided so that when the belts are secured to the keel as illustrated in FIG. 1, by means of screws 23 or the like, the outer surfaces 24 of the belts lie substantially flush with the surfaces of the keel.

The two members or plates 20 and 21 are shaped as illustrated and thus define a wedge shaped cavity 25 therebetween which is filled with flexible plastic 26 having a relatively high durometer reading. By preforming the belts to the shape illustrated and then filling same with the plastic 26, this formation is maintained and it will be seen that, when viewed in side elevation, the toe assembly curves upwardly in a substantial continuation of the curvature of the instep portion 14.

The distal ends 27 are bonded together or in very slightly spaced relationship by the plastic 26 when formed. This plastic may be in the form of hard foam or any desired form of flexible plastic depending upon design parameters.

Once the keel and toe assembly are formed, these may be surrounded by a one-piece flexible foam foot shaped body 12 preferably moulded in a rubber or similar mould by a process which utilizes room temperature for curing, and which produces a smooth exterior skin.

The type of moulding is well known in the art and the rubber mould may be formed from vulcanized rubber which is also well known in the art.

By providing this particular type of moulding, the part line, instead of being part way up the body, may be situated at the sole line 28 thus giving a smooth, continuous skin effect to the finished foot. Needless to say the color of the outer body portion may be determined as desired. Note from FIG. 5 that sole line 28 is further concealed by being at the inner limit of curvature of the side of the assembly.

When the body 12 is moulded around the keel and toe assemblies 10 and 11, a vertical cylindrical bore 29 is provided immediately below an enlargement of bore 17 in the keel (identified by reference character 17A) thus allowing access for the bolt (not illustrated) used to attach the foot.

Also to facilitate the attachment of the foot, it will be observed that the keel and toe assembly are completely enveloped by the body 12 with the exception of a portion 13A of the upper planar surface 13 surrounding the drilling 17.

The aforementioned striations 19 formed on the outer surfaces of the keel 10 facilitate the adhesion of the foamed plastic or foamed rubber forming the body 12 and in this regard the durometer reading of the foamed plastic or foamed rubber forming the body 12 is less than the durometer reading of the plastic 26 of the toe assembly.

The angle of inclination of the surface of the diminished heel 15, is such that it gives a relatively deep heel portion 30 to the body 12 thus giving the desired cushioning effect when in use.

Also of importance is the fact that the body extends upwardly over the rear side 31 of the keel and that the thickness of the body behind the rear surface 31 diminishes to approximately ⅛ inches adjacent the upper surface 13 of the keel. Although this dimension can be varied from between 1/16 inches and ½ inches, nevertheless approximately ⅛ inches is the desirable thickness. This prevents displacement of the keel from the body, a fault that often occurs with conventionally built SACH feet.

The smooth skinned surface of the body 12 not only gives good wear characteristics and moisture repellancy characteristics but also facilitates the donning and doffing of socks, stockings, shoes and the like and presents a foot which is not unsightly when in use.

Finally, although a variety of synthetic foamed plastic or rubber compounds may be utilized both for the plastic insert 26 and the body 12, nevertheless polyurethane foams have been found to have excellent characteristics.

Since various modifications can be made in our invention as hereinabove described, and many apparently widely different embodiments of same made within the spirit and scope of the claims without departing from such spirit and scope, it is intended that all matter contained in the accompanying specification shall be interpreted as illustrative only and not in a limiting sense.

What we claim as our invention is:

1. A prosthetic foot comprising in combination a substantially rigid keel, said keel including a substantially flat upper attachment portion, a concavely curved instep portion, a nose portion, and a diminished heel portion, a toe assembly secured to and extending forwardly from the front ends of the instep portion and the diminished heel portion and enclosing said nose portion, and a one-piece, flexible foam, foot-shaped body with smooth exterior skin surrounding and enveloping said keel and said toe assembly, said toe assembly including upper and lower flexible plate members secured by one end thereof to said front ends and extending forwardly therefrom and converging together at the distal ends thereof to define a wedge shaped cavity therebetween, a foam insert moulded within said cavity thereby providing the necessary resistance to dorsiflexion of the foot when in use, the durometer reading of said foam insert being greater than the durometer reading of the said body.

2. The invention according to claim 1 in which part of the upper attachment portion is exposed to facilitate attachment of the foot.

3. The invention according to claim 1 in which the front end of the instep portion and the front end of the diminished heel portion are recessed to receive said one end of said flexible members whereby the outer surfaces of said flexible members are substantially flush with the outer surfaces of said front ends.

4. The invention according to claim 2 in which the front end of the instep portion and the front end of the diminished heel portion are recessed to receive said one end of said flexible members whereby the outer surfaces of said flexible members are substantially flush with the outer surfaces of said front ends.

5. The invention according to claim 1 in which said upper and lower flexible plate members and said foam insert therebetween form an upwardly curved wedge shaped configuration when installed on said keel and viewed in side elevation, the bonding of said foam insert to said upper and lower flexible plate members preforming the configuration of said toe assembly, the majority of the exposed surface of said rigid keel being striated to assist in the attachment of said one piece foam body thereto, said nose portion also being striated to assist in bonding the foam insert.

6. The invention according to claim 2 in which said upper and lower flexible plate members and said foam insert therebetween form an upwardly curved wedge shaped configuration when installed on said keel and viewed in side elevation, the bonding of said foam insert to said upper and lower flexible plate members preforming the configuration of said toe assembly, the majority of the exposed surface of said rigid keel being striated to assist in the attachment of said one piece foam body thereto, said nose portion also being striated to assist in bonding the foam insert.

7. The invention according to claim 3 in which said upper and lower flexible plate members and said foam insert therebetween form an upwardly curved wedge shaped configuration when installed on said keel and viewed in side elevation, the bonding of said foam insert to said upper and lower flexible plate members preforming the configuration of said toe assembly, the majority of the exposed surface of said rigid keel being striated to assist in the attachment of said one piece foam body thereto, said nose portion also being striated to assist in bonding the foam insert.

8. The invention according to claim 4 in which said upper and lower flexible plate members and said foam insert therebetween form an upwardly curved wedge shaped configuration when installed on said keel and viewed in side elevation, the bonding of said foam insert to said upper and lower flexible plate members preforming the configuration of said toe assembly, the majority of the exposed surface of said rigid keel being striated to assist in the attachment of said one piece foam body thereto, said nose portion also being striated to assist in bonding the foam insert.

9. The invention according to claim 1 in which the portion of said one piece foam body portion increases in thickness below said diminished heel portion of said keel, from the front thereof towards the rear thereof and extends upwardly behind said keel to the rear side of said upper attachment portion, the thickness of said body at the rear of said keel decreasing to a dimension between 1/16 inches and ½ inches at the said upper attachment portion.

10. The invention according to claim 2 in which the portion of said one piece foam body portion increases in thickness below said diminished heel portion of said keel, from the front thereof towards the rear thereof and extends upwardly behind said keel to the rear side of said upper attachment portion, the thickness of said body at the rear of said keel decreasing to a dimension between 1/16 inches and ½ inches at the said upper attachment portion.

11. The invention according to claim 3 in which the portion of said one piece foam body portion increases in thickness below said diminished heel portion of said keel, from the front thereof towards the rear thereof and extends upwardly behind said keel to the rear side of said upper attachment portion, the thickness of said body at the rear of said keel decreasing to a dimension between 1/16 inches and ½ inches at the said upper attachment portion.

12. The invention according to claim 4 in which the portion of said one piece foam body portion increases in thickness below said diminished heel portion of said keel, from the front thereof towards the rear thereof and extends upwardly behind said keel to the rear side of said upper attachment portion, the thickness of said body at the rear of said keel decreasing to a dimension between 1/16 inches and ½ inches at the said upper attachment portion.

13. The invention according to claim 5 in which the portion of said one piece foam body portion increases in thickness below said diminished heel portion of said keel, from the front thereof towards the rear thereof and extends upwardly behind said keel to the rear side of said upper attachment portion, the thickness of said body at the rear of said keel decreasing to a dimension between 1/16 inches and ½ inches at the said upper attachment portion.

14. The invention according to claim 6 in which the portion of said one piece foam body portion increases in thickness below said diminished heel portion of said keel, from the front thereof towards the rear thereof and extends upwardly behind said keel to the rear side of said upper attachment portion, the thickness of said body at the rear of said keel decreasing to a dimension between 1/16 inches and ½ inches at the said upper attachment portion.

15. The invention according to claim 7 in which the portion of said one piece foam body portion increases in thickness below said diminished heel portion of said keel, from the front thereof towards the rear thereof and extends upwardly behind said keel to the rear side of said upper attachment portion, the thickness of said body at the rear of said keel decreasing to a dimension between 1/16 inches and ½ inches at the said upper attachment portion.

16. The invention according to claim 8 in which the portion of said one piece foam body portion increases in thickness below said diminished heel portion of said keel, from the front thereof towards the rear thereof and extends upwardly behind said keel to the rear side of said upper attachment portion, the thickness of said body at the rear of said keel decreasing to a dimension between 1/16 inches and ½ inches at the said upper attachment portion.

* * * * *